(12) United States Patent
Eskandar et al.

(10) Patent No.: US 7,725,192 B2
(45) Date of Patent: May 25, 2010

(54) METHODS OF INCREASING LEARNING RATE

(75) Inventors: Emad Eskandar, Nahant, MA (US); Ziv Williams, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 320 days.

(21) Appl. No.: 11/545,808

(22) Filed: Oct. 10, 2006

(65) Prior Publication Data

US 2007/0225774 A1    Sep. 27, 2007

Related U.S. Application Data

(60) Provisional application No. 60/725,771, filed on Oct. 12, 2005.

(51) Int. Cl.
*A61N 1/00* (2006.01)

(52) U.S. Cl. ....................................................... 607/45
(58) Field of Classification Search .................... 607/45
See application file for complete search history.

(56) References Cited

U.S. PATENT DOCUMENTS

| 6,234,953 | B1 | 5/2001 | Thomas et al. | |
|---|---|---|---|---|
| 6,400,978 | B1 * | 6/2002 | Teicher et al. | ................ 600/410 |
| 6,539,263 | B1 | 3/2003 | Schiff et al. | |
| 6,556,868 | B2 | 4/2003 | Naritoku et al. | |
| 6,708,064 | B2 * | 3/2004 | Rezai | .......................... 607/45 |
| 2002/0076398 | A1 | 6/2002 | Filippo et al. | |
| 2002/0087201 | A1 | 7/2002 | Firlik et al. | |
| 2002/0091419 | A1 | 7/2002 | Firlik et al. | |
| 2002/0169485 | A1 | 11/2002 | Pless et al. | |
| 2003/0097159 | A1 | 5/2003 | Schiff et al. | |
| 2003/0097161 | A1 | 5/2003 | Firlik et al. | |
| 2005/0154425 | A1 | 7/2005 | Boveja et al. | |
| 2006/0004422 | A1 * | 1/2006 | De Ridder | .................... 607/45 |
| 2006/0212090 | A1 * | 9/2006 | Lozano et al. | ................. 607/45 |
| 2009/0076567 | A1 * | 3/2009 | Fowler et al. | ................. 607/45 |

FOREIGN PATENT DOCUMENTS

| WO | WO 03/091694 A2 | 4/2003 |
|---|---|---|
| WO | WO 2005/087314 A1 | 9/2005 |

OTHER PUBLICATIONS

Alexander, G.E. & Delong, M.R., Microstimulation of the primate neostriatum. II. Somatotopic organization of striatal microexcitable zones and their relation to neuronal response properties. J Neurophysiol. Jun. 1985;53(6):1417-30.

Almaguer, W. et al., Post-training stimulation of the basolateral amygdala improves spatial learning in rats with lesion of the fimbria-fornix. Restor Neurol Neurosci. 2005;23(1):43-50.

(Continued)

*Primary Examiner*—Scott M Getzow
(74) *Attorney, Agent, or Firm*—Wolf, Greenfield & Sacks, P.C.

(57) ABSTRACT

The invention relates, in part, to methods of administering electrical or magnetic brain stimulation to increase learning rate.

18 Claims, 8 Drawing Sheets

OTHER PUBLICATIONS

Aosaki, T. et al., Temporal and spatial characteristics of tonically active neurons of the primate's striatum. J Neurophysiol. Mar. 1995;73(3):1234-52.

Cavanaugh, J.R. et al., Nature and interaction of signals from the receptive field center and surround in macaque V1 neurons. J Neurophysiol. Nov. 2002;88(5):2530-46.

Cohen, M.R. & Newsome, W.T., What electrical microstimulation has revealed about the neural basis of cognition. Curr Opin Neurobiol. Apr. 2004;14(2):169-77. Review.

Hadj-Bouziane, F. & Boussaoud, D., Neuronal activity in the monkey striatum during conditional visuomotor learning. Exp. Brain Res. Nov. 2003;153(2):190-6. Epub Aug. 28, 2003.

Hernandez-Lopez, S. et al., D1 receptor activation enhances evoked discharge in neostriatal medium spiny neurons by modulating an L-type Ca2+ conductance. J Neurosci. May 1, 1997;17(9):3334-42.

Hollander, E. et al., Striatal volume on magnetic resonance imaging and repetitive behaviors in autism. Biol Psychiatry. Aug. 1, 2005;58(3):226-32.

Hollerman, J.R. et al., Influence of reward expectation on behavior-related neuronal activity in primate striatum. J Neurophysiol. Aug. 1998;80(2):947-63.

Houk, J.C. et al., MIT Press, Cambridge, MA 1995. Models of Information Processing in the Basal Ganglia, Chapter 11: 216-232.

Jahanshahi, M. et al., The impact of deep brain stimulation on executive function in Parkinson's disease. Brain. Jun. 2000;123 ( Pt 6):1142-54.

Jog, M.S. et al., Building neural representations of habits. Science. Nov. 26, 1999;286(5445):1745-9.

Kawagoe, R. et al., Expectation of reward modulates cognitive signals in the basal ganglia. Nat Neurosci. Sep. 1998;1(5):411-6.

Knecht, S. et al., Levodopa: faster and better word learning in normal humans. Ann Neurol. Jul. 2004;56(1):20-6.

Miyachi, S. et al., Differential roles of monkey striatum in learning of sequential hand movement. Exp Brain Res. Jun. 1997;115(1):1-5.

O'Doherty, J. et al., Dissociable roles of ventral and dorsal striatum in instrumental conditioning. Science. Apr. 16, 2004;304(5669):452-4.

O'Doherty, J.P. Reward representations and reward-related learning in the human brain: insights from neuroimaging. Curr Opin Neurobiol. Dec. 2004;14(6):769-76. Review.

Pasupathy, A. & Miller, E.K., Different time courses of learning-related activity in the prefrontal cortex and striatum. Nature. Feb. 24, 2005;433(7028):873-6.

Reynolds, J.N. et al., A cellular mechanism of reward-related learning. Nature. Sep. 6, 2001;413(6851):67-70.

Schraudolph, N.N. et al., Fast curvature matrix-vector products for second-order gradient descent. Neural Comput. Jul. 2002;14(7):1723-38.

Schultz, W. Predictive reward signal of dopamine neurons. J Neurophysiol. Jul. 1998;80(1):1-27. Review.

Shohamy, D. et al., The role of dopamine in cognitive sequence learning: evidence from Parkinson's disease. Behav Brain Res. Jan. 30, 2005;156(2):191-9.

Singh, V.K. & Rivas, W.H., Prevalence of serum antibodies to caudate nucleus in autistic children. Neurosci Lett. Jan. 23, 2004;355(1-2):53-6.

Smith, A.C. et al., Dynamic analysis of learning in behavioral experiments. J Neurosci. Jan. 14, 2004;24(2):447-61. Erratum in: J Neurosci. Mar. 23, 2005;25(12):table of contents.

Suri, R.E. & Schultz, W., A neural network model with dopamine-like reinforcement signal that learns a spatial delayed response task. Neuroscience. 1999;91(3):871-90.

Suzuki, T. et al., Dopamine-dependent synaptic plasticity in the striatal cholinergic interneurons. J Neurosci. Sep. 1, 2001;21(17):6492-501.

Tehovnik, E.J., Electrical stimulation of neural tissue to evoke behavioral responses. J Neurosci Methods. Mar. 1996;65(1):1-17. Review.

Wickens, J.R. et al., Neural mechanisms of reward-related motor learning. Curr Opin Neurobiol. Dec. 2003;13(6):685-90. Review.

Williams, Z. and Eskandar, E.N. Neuronal Correlates of Associative Learning in the Primate Striatum and Its Selective Enhancement by Electrical Stimulation: 819. Abstracts of Open Papers. Congress of Neurological Surgeons, 2005, Boston, MA.

Wirth, S. et al., Single neurons in the monkey hippocampus and learning of new associations. Science. Jun. 6, 2003;300(5625):1578-81.

* cited by examiner

METHODS OF INCREASING LEARNING RATE

RELATED APPLICATIONS

This application claims priority under 35 U.S.C. §119(e) from U.S. provisional application Ser. No. 60/725,771, filed Oct. 12, 2005, the entire content of which is incorporated by reference herein.

GOVERNMENT SUPPORT

The invention was made with government support under grant number 5K08NS41851 awarded by the National Institutes of Neurological Disorders and Stroke (NINDS). The United States Government has certain rights in the invention.

FIELD OF THE INVENTION

The invention relates, in part, to methods of increasing a rate of learning using electrical or magnetic brain stimulation.

BACKGROUND OF THE INVENTION

The mechanisms underlying the formation of visual-motor associations, and the role of dopamine in this process, are topics of great importance in neuroscience. Derangements of this circuitry may play a role in Parkinson's Disease (PD) and learning disorders such as autism. There are numerous studies indicating that patients with PD suffer from learning deficits. In one such study, patients with PD were found to have impairments in sequence learning that were reversed with the administration of the dopamine precursor levodopa (Shohamy, D. et al., Behav Brain Res. 156:191-199, 2005). In support of the role of dopamine in learning, a recent study found that in normal human subjects, levodopa significantly enhanced the speed, overall success, and long-term retention of novel word learning in a dose-dependent manner (Knecht, S. et al., Ann Neurol. 56: 20-26, 2004). In addition, there is increasing evidence that striatal dysfunction may be an important component of autism. Volumetric MRI studies have suggested that there are differences in caudate size between normal and autistic children (Hollander, E. et al., Biol Psychiatry 58: 226-232, 2005). Other studies have suggested that autistic children may have increased serum antibodies to the caudate nucleus (Singh, V. K. & Rivas, W. H., Neurosci Lett. 355: 53-56, 2004), but the role of specific brain regions in learning such as the formation of visual-motor association remains unclear.

SUMMARY OF THE INVENTION

The invention relates, in part, to methods of increasing the rate of learning in subjects by administering electrical or magnetic brain stimulation, for example deep brain stimulation, to the subject during learning intervals. Surprisingly, it has been identified that the administration of deep brain stimulation to regions of the brain such as the caudate during intervals of reinforcement in learning results in a faster acquisition of the learned behavior.

According to one aspect of the invention, methods for increasing the rate of learning in a subject are provided. The methods include electrically or magnetically stimulating a brain region of the subject during an interval of learning in the subject. In some embodiments, the learning comprises formation of a visual-motor association. In some embodiments, the interval of learning comprises a reinforcement interval. In certain embodiments, the reinforcement interval comprises a feedback period of learning. In some embodiments, the brain region is the striatum. In some embodiments, the brain region is the caudate. In certain embodiments, the brain region is the anterior caudate. In some embodiments, the stimulation of the brain region comprises deep brain stimulation. In some embodiments, the deep brain stimulation comprises high frequency microstimulation. In some embodiments, the high frequency microstimulation is at a pulse frequency of about 200 Hz. In certain embodiments, the high frequency microstimulation is at a phase length of about 0.2 ms. In some embodiments, the high frequency microstimulation is at an interphase interval of about 0.2 ms. In certain embodiments, In some embodiments, the high frequency microstimulation is at an amperage of about 200 µA. In some embodiments, the high frequency microstimulation comprises a stimulus train of about 1000 ms. In certain embodiments, the stimulation of the brain region comprises transcranial magnetic stimulation. In some embodiments, the stimulation of the brain region comprises epidural electrical stimulation. In some embodiments, the subject has, has had, or is suspected of having a neurological disease or disorder. In some embodiments, the subject does not have and/or has not had a neurological disease or disorder. In some embodiments, the neurological disease or disorder is associated with a deficit in learning. In some embodiments, the neurological disease or disorder is a associated with a deficit in the formation of visual-motor associations. In certain embodiments, the neurological disease or disorder is an associative learning disorder, a brain injury, a neurodegenerative disorder, stroke, epilepsy, autism, or Parkinson's disease. In some embodiments, the subject is a primate. In some embodiments, the subject is a human.

These and other objects of the invention will be described in further detail in connection with the detailed description of the invention.

BRIEF DESCRIPTION OF THE DRAWINGS

FIG. 1A is a schematic illustration and time-line of events for the main task. FIG. 1B is a peri-event histogram and rasters for two single neurons over the course of one learning block while the animal learned to associate a novel image with a movement toward a specific target-location. Activity is aligned to the feedback tone (first dashed line). Each row in the raster represents a single trial, with the trial numbers shown on the left. The black squares on the right indicate correct trials and the arrowheads indicate the trial at which the learning criterion was reached. FIG. 1C shows learning performance and mean neuronal activity during the feedback period. The blue line indicates the animals' behavioral performance, or learning curve, with the dashed lines representing the upper and lower confidence bounds (99%) estimated from the animals' performance. The red line represents the learning rate (first derivative or slope of the learning curve). The black line represents the average firing rate for the cell during the feedback period. On the left plot, neuronal activity closely correlates with the learning curve, whereas on the right plot, neuronal activity correlates more closely with the learning rate. The arrowheads indicate the trial at which learning criterion was reached.

FIG. 2A shows results of correlation coefficients were calculated for the population of caudate cells (N=153) by comparing neuronal activity during each 500 ms time period (i.e. image, delay, feedback) with either the learning curve (blue line), or learning rate (red line). Each point along the curve represents the mean r-value for the population during that time period. Asterisks indicate intervals during which the distribution of r-values was significantly different from chance ($p<0.01$). Error bars indicate s.e.m. FIG. 2B shows the distribution of learning curve and learning rate-related r-values for all caudate cells at the time of feedback. Black bars indicate cells with significant r-values ($p<0.01$). The lower and upper arrows indicate the mean learning curve-related and learning rate-related r-values, respectively, for the population. FIG. 2C shows results indicating mean neuronal activity for the population of caudate cells, and behavioral performance aligned to learning criterion (trial 0). The blue line represents the learning curve and the red line represents the learning rate, averaged across all trials (confidence bounds not shown). The black line represents mean neuronal activity during the feedback period minus baseline, with error bars indicating s.e.m. Only cells with either significant learning curve or learning rate-related activity were included in this plot. FIG. 2D illustrates the distribution of lag times for learning criteria between neuronal responses and behavioral performance for each cell. A negative trial number indicates that neuronal criterion was achieved before behavioral criterion, whereas a positive trial number indicates that it was achieved after. The blue and red arrows indicate the mean lag for cells with learning curve-related and learning rate-related r-values, respectively. FIG. 2E shows the locations of all recording sites within the caudate. Zero indicates the level of the anterior commissure in the A-P dimension, midline in the M-L dimension, and the dorsal margin of the caudate in depth. The color codes indicate the mean learning rate-related neuronal response ($r_r$) for each site. FIG. 2F illustrates mean activity during feedback for putaminal cells, with the same convention as in FIG. 2C.

FIG. 3A shows results from monkey P (N=124; $r_r$=0.26, $p<0.0000001$), and FIG. 3B shows results from monkey N (N=29; $r_r$=0.29, $p<0.0001$).

FIG. 4A shows results when correlation coefficients were calculated for the population of caudate cells by comparing neuronal activity during each time period of the task with the learning rate. Each point along the curve represents the mean r-value for the population during that time period for positively correlated cells (solid line, N=112), and negatively correlated cells (dashed line, N=41). FIG. 4B shows results of mean neuronal activity for the population of caudate cells for each animal, and behavioral performance aligned to learning criterion (trial 0). The blue line represents the learning curve and the red line represents the learning rate, averaged across all trials. The black line represents mean neuronal activity during the feedback period minus baseline for cells with a positive correlation (solid line) and negative correlation (dashed line) to the learning rate. Error bars indicate s.e.m.

FIG. 5A shows results from monkey P (N=51 images; $SI_r$=0.19, $p<0.01$) and FIG. 5B shows results from monkey N (N=10 images; $SI_r$=0.25, $p<0.05$).

FIG. 6A shows learning curves that are aligned to the first correct trial (0). The top line represents mean performance for novel images in which high frequency microstimulation (HFM) was delivered in the caudate following correct responses during the reinforcement period (triggered at feedback). The bottom line represents mean performance for novel images in which no stimulation was delivered. Error bars indicate s.e.m (61 novel images per curve). Thick areas along the top curve indicate trial-points at which performance on stimulated trials was significantly different from performance on non-stimulated trials ($p<0.05$). FIG. 6B shows the distribution of learning criteria for stimulated and non-stimulated images, with the blue line representing mean performance for novel images in which high frequency microstimulation (HFM) was delivered in the caudate following correct responses during the reinforcement period (triggered at feedback) and the black line representing mean performance for novel images in which no stimulation was delivered. The abscissa indicates the total number of trials (beginning with the first correct trial) it took the animals to reach learning criterion. The arrowheads indicate the average number of trials to reach criterion for all images in each set. FIG. 6C shows the locations of all stimulation sites within the caudate. Zero indicates the level of the anterior commissure in the A-P dimension, midline in the M-L dimension, and the dorsal margin of the caudate in depth. The color codes indicate the mean $SI_r$ obtained from stimulation at each site.

FIGS. 7A-D show learning curves that are aligned to the first correct trial (0). Microstimulation trains were triggered either on feedback or on image presentation, depending on the experiment type (indicated in plot title). The solid colored lines in each figure represent the animals' performance for trials in which stimulation was delivered for one of the two concurrently learned novel images. The dashed lines, with their corresponding color codes, represent the animals' performance for the concurrently learned non-stimulated novel images. The black line represents trials in which no stimulation was delivered for either of the two novel images (baseline). Error bars (s.e.m) are displayed only on the black curve for clarity. Thick areas along the curves indicate trial-points at which performance on stimulated trials was significantly different from baseline ($p<0.05$). The legend in the right-bottom of each figure indicates the color code for each task types. The number of learning blocks used to construct each curve is indicated in parenthesis. All curves within each figure were obtained from interleaved trial sets performed within the same task sessions. FIG. 7A provides a comparison of low and high frequency stimulation in the caudate. The black and blue curves in FIG. 7A are the same as those shown in FIG. 6A. FIG. 7B shows results from stimulation in the caudate during correct trials, incorrect trials, or both. FIG. 7C shows results of stimulation in the caudate during the image presentation epoch. FIG. 7D shows results of stimulation in the putamen during the feedback epoch.

DETAILED DESCRIPTION OF THE INVENTION

Figure 1:
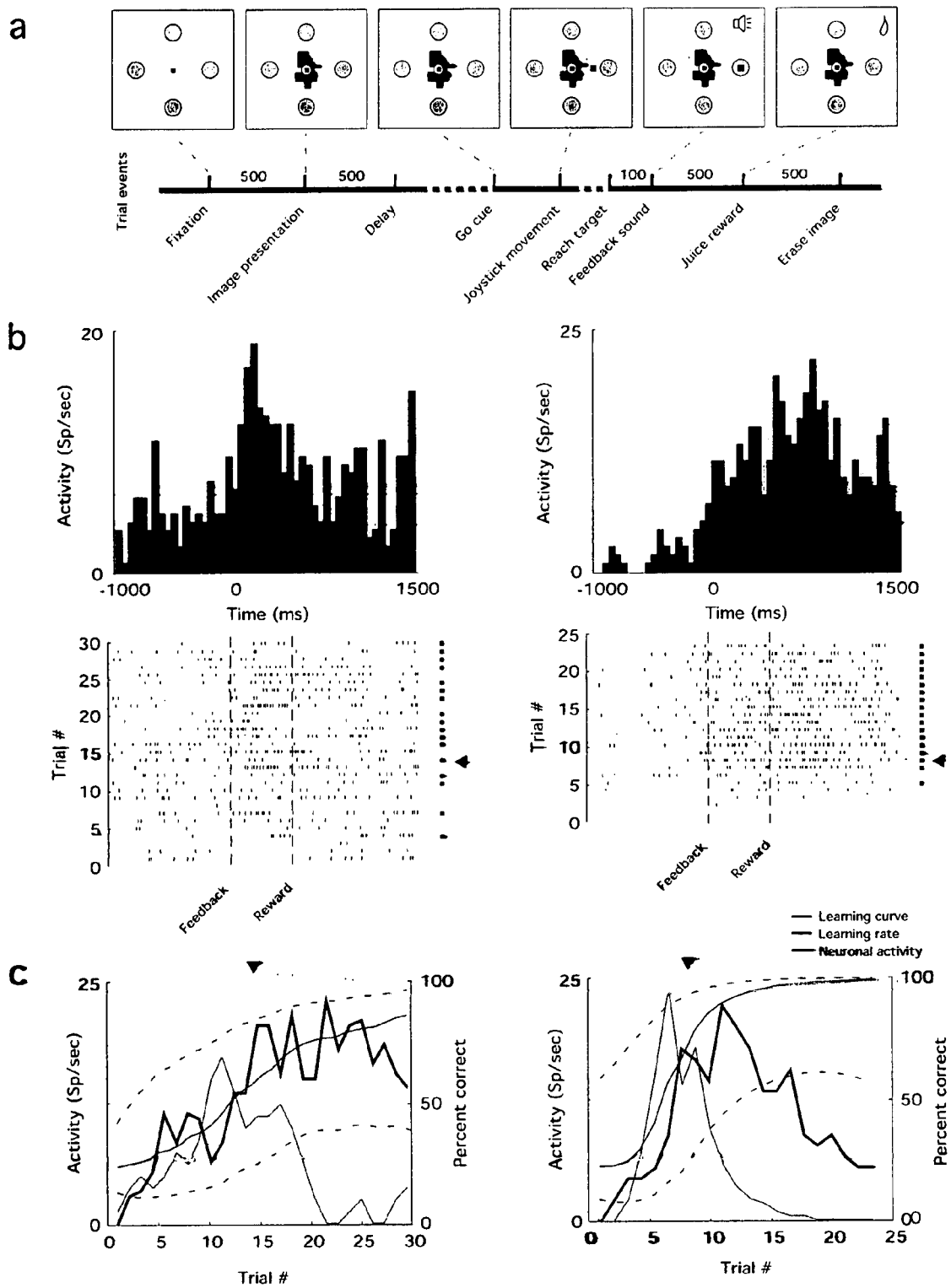
FIG. 1 shows schematic diagrams and graphs illustrating single neuronal responses during learning.

Primates have the remarkable ability to rapidly associate particular sensory cues with specific behaviors. For example, seeing a predator means running away, but seeing an appetizing fruit may initiate feeding behavior. It has now been discovered that neuronal activity in a part of the brain known as the caudate nucleus plays a role in this process. In particular, it has now been demonstrated that this area is responsible for modifying or adjusting behavioral responses to particular stimuli in order to maximize the chance of obtaining reward. Moreover, it has been discovered that delivering electrical stimulation to brain regions during specific time intervals can significantly enhance the rate of learning. This effect is reproducible and highly selective for specific associations. These findings are important in allowing the modification and/or enhancement of learning. Such a technique may be used to enhance treatment of neurological diseases and/or disorders, including, but not limited to: brain injury due to stroke or trauma, degenerative disorders such as Parkinson Disease, and learning disorders such as autism. Techniques of the invention may also be used to enhance learning in subjects without a neurological disease or disorder, e.g., a subject with a learning rate and/or ability that is normal or above normal.

In some aspects the invention includes methods for increasing the rate of learning in a subject. Learning may be generally viewed as the acquisition of a response (e.g., a behavior or action, etc.) by a subject that occurs in response to a triggering event. The rate at which the subject learns to associate the triggering event with the proper or correct response is the rate of learning for that task. One example of a type of learning that may be enhanced by the methods of the invention is visual-motor associative learning. In visual-associative learning a subject adjusts or modifies associations between visual cues and specific responses, e.g., motor responses, etc. Thus, in one example of visual-associative learning, a subject may learn to associate a novel visual image with a specific task. When the subject performs the task correctly, a feedback cue is provided to the subject followed by a reward for the subject. Neuronal responses during the different periods of a task (e.g., during the cue, activity, feedback, or reward interval) may be examined as a function of the subjects' trial-by-trial performance, or learning curve for the subject. The slope of the learning curve is referred to herein as the learning rate and it represents the speed at which a new association is learned by a subject. An increase in leaning rate may be a statistically significant increase in the learning rate for a subject. Methods for determining and assessing the rate of learning in a subject are provided herein and also may include additional art-known methods for such determinations.

The invention relates in part to the discovery that the administration of electrical or magnetic stimulation to the brain of a subject during a learning interval such as the feedback or reward interval of learning (e.g., the reinforcement interval) increases the rate of learning of a task by the subject.

As used herein a subject is preferably a mammal and may be a human or non-human primate. Additionally a subject of the invention may be a dolphin, dog, horse, cat, or rodent, etc. In some aspects of the invention, a subject is known to have, or is considered to be at risk of having, a disease or disorder associated with a learning deficit. In some embodiments, a subject is a mammal that is an animal model for a neurological disease or disorder that is associated with a learning deficit. One of ordinary skill in the art will recognize that animal models of a learning deficit-associated disease or disorder may be generated by genetic engineering or by chemical or physical treatment (e.g., stroke models, PD models, etc.). In some aspects of the invention, a subject is a mammal that has no known or predicted learning deficit or abnormality.

A subject to whom the methods of the invention may be applied may include a subject who has currently or has previously had a neurological disease or disorder. In addition, a subject may be suspected of having a neurological disease or disorder or may be considered by one of skill in the medical arts to be at risk or at an elevated risk of having a neurological disease or disorder. A neurological disease or disorder may include, but is not limited to diseases and disorders associated with a learning deficit, such as, but not limited to diseases or disorders that include a deficit in the formation of visual-motor associations. A neurological disease or disorder may include but is not limited to an associative learning disorder, a brain injury, a neurodegenerative disorder, stroke, epilepsy, autism, or Parkinson's disease.

Methods of the invention may also be applied to a subject with no known, suspected, or predicted neurological disease or disorder. Thus a suitable subject for the methods for method of the invention may have no learning deficit and may have a normal or above-normal learning rate and/or ability. In such subjects, methods of the invention may be useful to enhance learning and/or rate of learning from a "normal" or "above normal" level or rate to a higher level and/or rate. Methods of the invention for enhancing learning may be used to enhance training in complex visual motor tasks in subjects with below normal, normal, or above-normal learning rate and/or ability. Non-limiting examples of complex visual motor tasks include piloting airplanes, use of advanced weapon systems, complex assembly work, etc.

The invention, in some aspects, includes electrical and/or magnetic stimulation of the brain of a subject. In the methods of the invention, stimulation may be administered to specific brain regions in the subject during an interval of learning. As use herein, an interval of learning may be a period of time in which the subject receives feedback or a reward. Feedback or reward are indications to the subject that the behavior or action of the subject in response to the training event, thus these are reinforcing events. An example of a training event for visual-motor learning is the visual event that the subject is to associate with the motor action. In such a visual-motor learning embodiment, the feedback or reward is received by the subject after the successful motor action (task) by the subject following the associated visual event. Using the methods of the invention, the administration of electrical or magnetic stimulation during the interval of feedback or reward can result in an increase in the rate of learning by the subject.

An example of a specific brain region that may be administered electrical and/or magnetic stimulation according to the methods of the invention is the striatal region of the brain. In some embodiments of the invention, the brain region to which magnetic or electrical stimulation is administered is the caudate nucleus. In certain embodiments, the brain region that is stimulated is the anterior or dorsal-anterior caudate region. In certain embodiments, the electrical and/or magnetic stimulation may be administered to the head of the caudate nucleus.

It will be understood that learning enhancing methods of the invention may be used in combination with one or more additional procedures and/or medications that are administered to a subject to enhance learning.

Electrical or magnetic stimulation of the brain and/or brain regions may be administered using various methods as described herein or known in the art. Deep brain stimulation can be used to administer electrical current to one or more specific brain regions. An alternative method of administering electrical stimulation to brain region(s) of a subject during a learning interval is through the use of epidural electrical stimulation. Magnetic stimulation of brain region(s) of a subject during an interval of learning can be administered use methods such as transcranial magnetic stimulation. Thus, various art-recognized methods of neural stimulation can be used in the claimed brain stimulation methods of the invention. Additional art-known methods of brain stimulation that allow stimulation of brain region(s) during learning intervals in a subject may also be used in the claimed methods.

With respect to electrical stimulation of the brain, the methods of the invention may include the use of deep brain stimulation. U.S. Pat. No. 6,920,359 describes systems for deep brain stimulation and the use of such methods for reducing movement disorders (e.g., tremor) in certain subjects. Deep brain stimulation methodology may be used in the methods of the invention to provide high frequency microstimulation to brain regions for the enhancement of learning, including, but not limited to, increasing the rate of learning. The invention includes, in some aspects, the administration of high frequency microstimulation with a pulse frequency of from about 150 Hz, 160 Hz, 170 Hz, 180 Hz, 190 Hz, 200 Hz, 210 Hz, 220 Hz, 230 Hz, 240 Hz to at least about 250 Hz. In some embodiments, the high frequency microstimulation is at a pulse frequency from about 190 Hz to about 210 Hz. In one preferred embodiment, the high frequency microstimulation is at a pulse frequency of about 200 Hz. A phase length of the microstimulation administered using methods of the invention may be from about 0.1 ms, 0.2 ms, 0.3 ms, 0.4 ms to about at least about 0.5 ms. For example, in some embodiments, the high frequency microstimulation is at a phase length of about 0.2 ms. An interphase interval of the high frequency microstimulation used in the methods of the invention may be from about 0.1 ms, 0.2 ms, 0.3 ms, 0.4 ms, to at least about 0.5 ms. For example, in some embodiments, the high frequency microstimulation is at an interphase interval of about 0.2 ms. In some aspects of the invention an amperage of high frequency microstimulation may be from about 100 µA, 150 µA, 200 µA, 250 µA, to at least about 300 µA. An example of an amperage of microstimulation useful in the methods of the invention is an amperage of about 200 µA. The high frequency microstimulation of the invention may include a stimulus train from about 500 ms, 600 ms, 700 ms, 800 ms, 900 ms, 1000 ms, 1100 ms, 1200 ms, 1300 ms, 1400 ms, 1500 ms, 1600 ms, 1700 ms, 1800 ms, 1900 ms, to at least about 2000 ms. In some embodiments, the high frequency microstimulation includes a stimulus train of about 1000 ms.

The invention involves, in part, the administration of an effective amount of electrical or magnetic stimulation to a region of the brain of a subject during a learning interval. The electrical or magnetic stimulation of the invention is administered in an effective amount and under parameters effective to increase the rate of learning in a subject. Typically effective amounts and effective parameters of electrical or magnetic stimulation can be determined in clinical trials using the methods described herein and/or as known by one of ordinary skill in the art, establishing an effective administration parameters (e.g., dose, frequency, timing, location, amperage, voltage, etc) for a test population versus a control population in a blind study. In some embodiments, an effective amount or parameter will be that amount and/or parameter that increases the rate of learning in a subject with a neurological disease or disorder. In some embodiments, an effective amount or parameter will be that amount and/or parameter that increases the rate of learning in a subject who has normal or above-normal learning rate before application or administration of methods of the invention. Thus, an effective amount or parameter may be the amount or parameter that when administered or used increases the rate of learning as from the amount that would occur in the subject without the administration of the electrical or magnetic stimulation to the brain region(s) of the subject.

The invention also involves, in part, the administration of an electrical or magnetic stimulation that increases the rate of learning in a subject as compared to the rate of learning in a control subject. The invention, in part, also relates to the administration of electrical or magnetic stimulation for the treatment of learning deficits in neurological diseases or disorders, brain injuries, learning disorders, etc. Methods of the invention, in part, may also relate to the administration of electrical or magnetic stimulation for the enhancement of learning rate in subjects without a learning deficit. As described herein, in some embodiments, a "control" rate may be a reference amount from a subject who has a neurological disease or disorder associated with a deficit in learning. An example of which, though not intended to be limiting, is a deficit in the formation of visual-motor associations or other types of learning. In some embodiments, a control rate may be a reference amount for from a subject who has no neurological disease or disorder associated with a deficit in learning. In some embodiments, a control rate may be a baseline learning rate for a subject. A baseline leaning rate may be the learning rate for a subject before the subject has been administered electrical or magnetic stimulation using a method of the invention. An increase in the rate of learning by a subject may be an increase in the rate of learning to a rate that is statistically significantly higher than that control amount.

In some cases, the increase in the rate of learning means the rate of learning is increased from an initial amount to a amount statistically significantly higher than the initial amount. In some embodiments, a control rate of learning may be the rate of learning in a subject not subjected to injury or disease. For example, one subject may be treated in such a way (e.g., chemically, genetically, or mechanically) as to induce neuronal injury or degeneration that is associated with a learning deficit and that subject may be then administered electrical or magnetic stimulation using the methods of the invention to assess the efficacy of the stimulation on the rate of learning in the subject. A control rate of learning in this example may be the amount present in a substantially similar subject that is not treated to induce injury or learning deficit.

It will be understood by one of ordinary skill in the art that a control rate of learning can be a predetermined value, which can take a variety of forms. It can be a single value, such as a median or mean. It can be established based upon comparative groups, such as in disease-free groups that have normal rates of learning. Other comparative groups may be groups of subjects with specific neurological disorders or disease, e.g., Parkinson's disease (PD); Alzheimer's Disease (AD); brain injury; autism; stroke; etc. Additional control groups may be groups of subjects known to not have a specific neurological disease or disorder that is associated with a learning deficit. It will be understood that disease-free subjects may be used as comparative groups for subjects that have a learning deficit that may be associated with a neurological disease or disorder. It will also be understood that disease-free subjects may be used as a comparative group for comparing normal, disease-free In some embodiments, electrical or magnetic stimulation that increases the rate of learning is an amount or regimen of electrical or magnetic stimulation that increases the rate of learning in a normal subject or increases the rate of learning in a subject with a disease or disorder that is associated with a learning deficit, for example a deficit in the formation of visual-motor associations.

The amount and manner of administration of an effective amount of electrical or magnetic stimulation to a region of the brain of a subject during a learning interval includes the determination of various administration parameters. Such parameters may include the frequency of the stimulation, amperage, time of stimulation train, location of stimulation in brain, region stimulated, etc. One of ordinary skill in the art will recognize that such parameters may be adjusted and tailored to an individual subject and can be assessed using the methods provided herein as well as additional art-known learning rate assessment methods.

The invention will be more fully understood by reference to the following examples. These examples, however, are merely intended to illustrate the embodiments of the invention and are not to be construed to limit the scope of the invention.

EXAMPLES

The ability of animals to learn arbitrary visual-motor associations is a topic of intense interest in neurobiology. Although neuronal correlates of learning have been identified within certain areas of the brain, the causal role of the observed activity has been, thus far, only speculative. This question has now been examined directly by using a unique two-pronged approach employing single-unit recordings and microstimulation in the dorsal striatum of primates actively performing an associative learning task. The results demonstrate, for the first time, that signals in the caudate nucleus appear to be responsible for dynamically modifying the 'associative weights' linking sensory cues and the animals' actual motor behavior. This is very distinct from previous studies in other areas demonstrating gradual changes in neuronal activity of the brain over the course of learning. Moreover, and of equal importance, we have made the remarkable discovery that delivering microstimulation in the anterior caudate at precise time intervals dramatically enhanced the animals' rate of learning—the effect was reproducible and highly selective for particular associations. These results may have profound implications for the comprehension of the mechanisms underlying learning, and may have important practical implications for understanding and treatment of learning disorders and neurological diseases and/or disorders.

Methods

Electrophysiology

Two adult male rhesus monkeys (*Macaca mulatta*) weighing 8 and 9 kg were used in the study. A titanium head post, plastic recording chamber and scleral search coil were surgically implanted following guidelines set by the animal review committee at Massachusetts General Hospital. The chamber was centered on the left side at stereotactic coordinates A16, L9 (interaural). All recording and stimulations both in the caudate and putamen was performed rostral to the anterior commissure. Magnetic resonance imaging (1.5 Tesla) was used to confirm target locations. Single unit recordings were made with tungsten microelectrodes that were advanced through a guide tube and grid system (Crist Instrument Company, Inc., Hagarstown, Md.) using a hydraulic micro-drive (David Kopf Instruments, Tujunga, Calif.). Neuronal activity was amplified, band-pass filtered between 200 Hz-5 kHz, and sampled at 20 kHz. Spikes were stored on a PC platform and sorted off-line using a template-matching algorithm (Spike 2, Cambridge Electronics Design, London UK). Electromyographic (EMG) activity was recorded using tin-disk surface electrodes placed below the jaw to ensure a broad and early detection of licking activity. Eye position, joystick position and EMG activity were each sampled and recorded at 1 kHz.

Stimulation Parameters

Biphasic stimulating pulses, with a cathodal phase leading, were delivered through a 300-600 k$\Omega$ tungsten microelectrode (Bak Electronics pulse generator and stimulus isolation unit) (Tehovnik, E. J. J Neurosci Methods. 65: 1-17, 1996). Phase length and interphase intervals were 0.2 ms, each. Pulse frequency was either 20 Hz (low frequency microstimulation) or 200 Hz (high frequency microstimulation) at 200 $\mu$A. Stimulus trains lasted for 1000 ms, and were triggered immediately following the feedback tone or image presentation depending on the experiment type. Stimulation epochs and durations were set to include either the reinforcement period (feedback and reward) or image presentation period (image presentation and delay). No explicit attempt was made to optimize the frequency or amplitude at which stimulation affected learning performance.

Learning Task

The animals were trained to perform a visual-motor associative learning task for 6-8 months prior to recordings. During the task, the animals were required to learn, by trial-and-error, to associate novel visual images displayed in the center of the monitor with a specific movement. The animals used a joystick to guide a cursor arising from the center of the screen to one of four targets displayed on the periphery of the screen. Each image was associated with only one rewarded target-location, and did not overlap with target-locations associated with the other images. Two of the images were randomly selected from a group of well-trained familiar images, and the other two from a group of randomly generated novel images that the animal had not previously seen. To ensure an even distribution of novel and familiar trials, each of the four images randomly appeared once within a set of four consecutive trials. After the animals completed a block of 18 correct trials for each image, a new set of images and target locations would be selected. This learning process was repeated multiple times for each cell.

Trials began with presentation of a central fixation point surrounded by four gray circular targets (distance 11° from the center). The animals were required to fixate within 1° of the fixation point for the entire trial. Once the animals fixated for 500 ms, a novel or familiar image would appear for 500 ms at the center of the screen, with the fixation point visible in the middle. After a variable delay of another 500-1000 ms, the fixation point would change color, at which time the monkeys used the joystick to move a cursor from the center of the screen to one of the targets. The cursor became visible when it was 3° away from the fixation point to limit smooth pursuit or saccadic eye movements. Once the cursor reached the target, another 100 ms would lapse, and then one of two feedback tones would sound indicating whether the animal had chosen the correct or incorrect target. The animals were then required to maintain the cursor within the target window for an additional 500 ms in order to receive the reward. If during a trial, the animal broke fixation, moved prematurely, or failed to maintain the cursor within the target circle (radial deflection in joystick of 2.5°), the trial would abort and no reward would be given. Once reward was delivered, 500 ms would lapse, the image would erase, and the sequence would repeat again. All trials in which the animal selected an incorrect target-location were repeated.

During these trials, neither monkey demonstrated a response bias to any particular direction of movement at the start of the trial block ($\chi^2$ test, p>0.05), and the animals rarely selected the same incorrect target two or more times in a row. Furthermore, no difference was found in the number of trials it took the animals to reach learning criterion between images that were presented first and images that were presented second during each learning block (rank-sum test, p>0.05).

Movement Activity

To control for potential activity associated with saccade planning or joystick movements, multiple novel images and associated target-locations were tested per cell. On average, for each cell recorded, 4.1±0.8 novel images were tested for each of the four target-locations or directions of movement. Novel images corresponding to each of the target-locations were also interleaved with an equal number of familiar images corresponding to the same target-locations on alternate trials.

In order to further limit the potential effects of joystick and eye movements, the animals were required to maintain eye fixation within a narrow window throughout the duration of the trial, and joystick position within the target window during feedback period in order for them to receive reward. In none of the recordings was there a systematic difference in mean eye position or cursor position during the feedback period when comparing trials before, during and after learning criterion (two-dimensional Kolmogorov-Smirnov test, p>0.05). Similarly, no difference was found in the mean magnitude or vector of movement (rank-sum test, p>0.05).

Finally, electromyographic licking activity was examined in one monkey for both the standard and replay control task (detailed below herein), and was found to begin on average 320 ms after reward delivery (2.5 SD above baseline, 50 ms windows at 10 ms increments). In no task type was there a correlation between the magnitude of licking activity during reward and the animals' rate of learning (bootstrap test, p>0.05).

Control Tasks

Guided-movement task. Animals performed alternating blocks of standard and control trials. In one block of trials, the monkeys performed the standard learning task. On the alternate block, a new pair of novel images was used. However, in these control trials the movement directions were 'copied' from the previous block, and were now indicated by a color change in one of the targets. The animals were previously trained to know that a change in color in one of the targets indicated the correct movement direction. Hence this did not constitute new learning. The sequence of image presentations, target selections, and reward delivery was the same as that of the previous standard task (including both correct and incorrect trials). Thus, as the trials progressed, novel images were repeatedly paired with movements to specific target-locations, but reward delivery was not contingent on the animals learning to associate the central visual image with a specific direction of movement. Trials that were aborted because of fixation breaks or premature movements during the standard task were not included in the control task.

In this task, the animals selected the colored target-location, even on non-rewarded trials, above 95% of the time. To examine whether or not the monkeys were actively learning new visual-motor associations during this control task, we tested one monkey with a third set of trials in which the color change that was previously used to instruct the monkeys' movements was now eliminated once the animal completed the control trial block. We found that this monkeys' performance fell to 23% after the color change was eliminated ($\chi^2$ test, p>0.05). The animal then took a similar number of trials to reach criterion as during the standard task, suggesting that the monkey had not learned the relevant visual-motor associations during the guided-movement control task.

Novelty Task. Animals performed alternating blocks of standard and control trials. Once the animal completed a block of trials for the standard learning task, the same two novel images were presented again in the following block. However, each image was now associated with a different target-location. In this manner, the animals had to learn a new visual-motor association but with the same set of images present. Blocks of standard and control trials were alternated such that an equal number of trials from each task type were recorded per cell.

Replay Task. Animals performed alternating blocks of standard and control trials. In the control trials, the exact same sequence of image presentations, cursor movements, feedback tones and reward delivery from the previous block of trials in the standard task were replayed to the monkeys but without the animal moving the joystick. During these trials, the animals were required to maintain their gaze on the central fixation spot in throughout the trial. If the monkeys moved the joystick at any time point during the trial, no reward would be given, and the trial would repeat.

Stimulation Trials

The monkeys performed the standard learning task as before, but with the introduction of stimulation trains during the feedback-reward time period. Stimulated trials were always interleaved with an equal number of concurrently learned non-stimulated trials. In this way, we could compare the effect of microstimulation on the learning of one novel image to that of a concurrently learned non-stimulated novel image. Blocks of trials were randomly interleaved such that stimulation was delivered during the feedback-reward epoch, or image presentation epoch, of correct trials alone, incorrect trials alone, or both correct and incorrect trials. In addition, we randomly interleaved learning blocks in which stimulation was delivered for one of the two novel images with learning blocks in which no stimulation was delivered for either of the novel images (baseline). For trials in which stimulation was delivered for incorrect trials alone, stimulation was delivered for all incorrect choices (i.e. all three incorrect target-locations).

In a separate set of control trials, the animals were presented with a fixation point but no central image and were then shown two randomly selected targets that changed color indicating that movement could start. Each pair of targets corresponded to the following combinations of reward and HFS delivery: reward alone vs. nothing, reward+HFS vs. reward alone, reward alone vs. HFS alone and HFS alone vs. nothing. On these trials, the animals were free to move to either of the two targets, and once 18 trials were completed, a new set of target-locations and reward/HFS contingencies was used.

Joystick and eye positions were continuously recorded during stimulation. Consistent with prior studies evaluating the affect of anterior striatal stimulation on movement (Alexander, G. E. & DeLong, M. R., J Neurophysiol. 53: 1417-1430, 1985), we found that stimulation did not alter mean cursor position or eye position within their target windows (2D Kolmogorov Smirnov test, p>0.05), nor did it alter the mean vector of movement at any time point during the task (rank-sum test, p>0.05). No stimulations were performed posterior to the anterior commissure in the "motor" sub-territory of the striatum.

Behavioral Analysis

The animal was considered to have successfully learned to associate a given novel image with the correct target-location once they had selected the correct target 5 or more times in a row. The probability of the animal having obtained this number of consecutive correct trials out of an average of 30 trials was 0.0192, and therefore unlikely to have occurred by chance. A state-space model was used to estimate the trial at which the animal had first learned the association, or had reached learning criterion (Smith, A. C. et al. J Neurosci. 24: 447-461, 2004; Wirth, S. et al., Science. 300: 1578-1581, 2003). We defined the learning criterion as the first trial in which the lower 99% confidence bounds obtained from the Gaussian state equation was greater than 0.25. That is, the animal was more than 99% likely to have successfully learned the correct visual-motor association on that trial. The criterion describes the point at which the animal has first successfully made the correct association, and occurs after the upslope of the learning curve when there is little further change in performance.

Learning criteria for neuronal responses were independently calculated for each cells by using a modification to the state-space model described previously (Smith, A. C. et al., J Neurosci. 24: 447-461, 2004; Wirth, S. et al., Science. 300: 1578-1581, 2003). Neuronal activity for cells with significant learning curve-related responses were compared to behavioral criterion obtained from the animals' performance for each stimulus. Criterion for cells with significant learning rate-related responses were obtained by calculating the integral, or area under the curve, of the response function, whereas criterion for cells with significant learning curve-related responses were obtained directly from the linear function of the response curve itself.

The mean behavioral performance, or learning curve, for each image was estimated from the animals' binary responses (correct/incorrect) using a Bernoulli probability model (Smith, A. C. et al., J Neurosci. 24: 447-461, 2004; Wirth, S. et al., Science. 300: 1578-1581, 2003). This provided a continuous estimate, ranging from 0 to 1, of the animals' performance. The learning rate was calculated by approximating the central difference derivative, which describes the slope, or rate of change, in the animals' performance (W. H Press, S. A. et al. Numerical Recipes in C++: The Art of Scientific Computing Cambridge Univ. Press, Cambridge, ed. 2, 2002). Therefore, the learning rate is lowest at the beginning and at the end of the learning curve when behavioral performance changes the least, and is highest at the steepest portion of the learning curve when performance changes the most.

Parametric analysis of behavioral performance was obtained by fitting the learning curves to a logistic equation using a $\chi^2$-minimization algorithm (Cavanaugh, J. R. et al., J Neurophysiol. 88: 2530-2546, 2002). Performance $P_k$ at trial number k=1, . . . , K, was defined by the equation:

$$P_k = P_i + \frac{P_f - P_i}{1 + \exp(-\gamma(k - \delta))}, \quad (S1)$$

where $P_i$ is defined as the initial performance, and $P_f$ is the final performance at the asymptotes. The rate-of-rise in the learning curve is governed by the constant $\gamma$, while the constant $\delta$ defines the inflection point of the curve. Three percent of the curves failed to converge to the function using a Levenberg-Marquardt modification to the fitting algorithm and were therefore excluded from further analysis (Schraudolph, N. N., Neural Comput. 14: 1723-1738, 2002). There was no difference in mean residual values between the task types indicating that the goodness-of-fit was similar across trial conditions (one-way ANOVA, p>0.05).

Selectivity indices (SI) for learning rate ($SI_r$) or final performance ($SI_{fp}$) on stimulation trials were defined as (A−B)/(A+B), with A and B being the values for each of the two trial conditions (stimulated vs. non-stimulated trials). Significance of change in SI was determined using a one-tailed t-test ($H_0$: SI=0, range −1 to 1; p<0.05). Thus, a learning rate SI ($SI_r$) of 0 would indicate that there is no difference in the rate of rise in performance ($\gamma$) between stimulated and non-stimulated trials. A positive $SI_r$ would indicate that the learning rate was higher on stimulated trials, whereas a negative $SI_r$ would indicate that the learning rate was lower.

Neuronal Activity

Peri-event histograms and rasters were constructed for all cells. Neuronal activity was aligned to image presentation onset, movement onset, feedback tone or reward delivery. To determine whether a cell was modulated by the task, activities for each 500 ms interval aligned to these events were compared to baseline at the time of fixation (repeated measures ANOVA, p<0.05). All cells were included for analysis regardless of whether they demonstrated significant peri-event activity. Cells with evidence of drift during baseline were not included at any point in the study (rank-sum test, p<0.05).

Auto-correlograms were also constructed for each cell, and individual action potentials examined from the neuronal tracings. Phasically active neurons corresponding to medium spiny projection neurons, and tonically active neurons corresponding to presumed cholinergic interneurons were classified by their characteristic firing pattern, and spike morphology as previously described (Alexander, G. E. & DeLong, M. R., J Neurophysiol. 53: 1417-1430, 1985; Aosaki, T. et al., J Neurophysiol. 73: 1234-1252, 1995).

Correlating Activity with Learning Performance

Firing rates during image presentation, movement, feedback and reward time periods (500 ms) were correlated to the animals' learning performance by aligning neuronal activity for each of the novel images to their corresponding learning criteria. Mean neuronal activity curves and behavioral performance curves were then obtained, and correlation coefficients (r) calculated from the aligned data. This allowed us to evaluate activity in each cell as a function of learning for multiple images and associated target-locations, before, during and after the criterion had been reached. Only neuronal activity for correct (rewarded) trials was included in this analysis. Incorrect trials were analyzed separately for control. In total, we found that learning-related responses in the majority of caudate cells were evident for multiple images and target-locations, with 91% of cells demonstrating learning rate-related responses to more than one novel image, and 72% of cells demonstrating learning rate-related responses across the four target-locations. In only 2% of neurons were responses found to correspond to only one target-location.

A bootstrap test was used to evaluate the significance of correlation between neuronal activity and behavioral performance for individual cells. In each cell, neuronal activity was randomly shuffled 1000 times across trials, and correlation coefficients recalculated from the shuffled data. If the rank of the calculated r-value was higher than 99% or lower than 1% of the shuffled distribution, then the correlation was considered to be significant.

Results

Primates have the remarkable ability to rapidly adjust or modify associations between visual cues and specific motor responses, such that profitable actions are more likely to be selected on subsequent iterations. While little is known as to how such adjustments in behavioral policy are implemented, recent learning models suggest that the dorsal striatum is optimally positioned to play a role in this process (Houk, J. C. et al., MIT Press, Cambridge Mass., 1995; Jog, M. S. et al., Science. 286: 1745-1749, 1999; O'Doherty, J. P. Curr Opin Neurobiol. 14: 769-776, 2004; O'Doherty, J. et al., Science. 304: 452-454, 2004; Reynolds, J. N. et al., Nature. 413: 67-70, 2001; Suri, R. E., & Schultz, W., Neuroscience. 91: 871-980, 1999; Wickens, J. R. et al., Curr Opin Neurobiol. 13: 685-690, 2003). We tested this idea directly by recording single-units and delivering microstimulation in the caudate and putamen of primates performing an associative learning task. Caudate activity during reinforcement was closely correlated with the rate of learning, and peaked during the steepest portion of the learning curve when new associations were being acquired. Moreover, delivering microstimulation in the caudate during the reinforcement period significantly increased the rate of learning without altering the animals' ultimate performance. This effect was highly selective for specific associations, and was not evident when stimulation was delivered in the putamen. These findings suggest that the caudate is responsible for implementing selective adjustments to the 'associative weights' between sensory cues and motor responses during learning, thus enhancing the likelihood of selecting profitable actions.

Two rhesus monkeys were trained to perform an associative learning task. During the task, the animals learned, by trial-and-error, to associate novel visual images with specific joystick movements in one of four radial directions (see Methods, above herein) In a given block of trials, four images were used. Two were randomly selected from a group of highly familiar images, and two were novel images that the animal had not seen before. A feedback tone was used to indicate whether or not the correct target was reached, which was then followed by the actual reward (FIG. 1A). An average of 16.5±0.6 novel images were presented for each recorded cell over numerous trial blocks, such that multiple images and associated target-locations were tested per cell. Of these, the animals learned 12.4±0.5 to criterion. Learning criterion was defined by the state-space approach, and was reached by the animals after an average of 4.1±0.2 (mean±s.e.m) consecutive correct trials (Smith, A. C. et al., J Neurosci. 24: 447-461, 2004; Wirth, S. et al., Science. 300: 1578-1581, 2003). The animals reached criterion after an average of 9.7±0.1 total trials (correct and incorrect).

One hundred seventy one cells were recorded from the dorsal-anterior caudate and 72 cells were recorded from the rostral putamen. Of these, 153 caudate, and 64 putaminal cells were classified as phasically active neurons (PANs), likely corresponding to medium spiny projection cells (Alexander, G. E. & DeLong, M. R., J Neurophysiol. 53: 1417-1430, 1985). Tonically active neurons were not included in the current analysis (Aosaki, T. et al., J Neurophysiol. 73: 1234-1252, 1995). The PANs recorded from the caudate are the main focus of this report, although the putaminal neurons provide an important contrast and will be discussed in that context.

Among caudate neurons, 23% were modulated during image presentation, 37% during movement, 39% during feedback and 40% during reward delivery (repeated measures ANOVA, $p<0.05$; FIG. 1B, Table 1). Table 1 shows results indicating neuronal modulation in the caudate and putamen. Each row in the table indicates the number and percent of cells modulated during each time period. The fifth row indicates the number and percent of cells modulated during any (one or more) of the four periods. The most prominent learning-related responses were observed during the feedback and reward periods. In 28% of neurons there was a gradual increase, and in 24% a gradual decrease in activity that plateaued once learning occurred (bootstrap test, $p<0.01$; FIG. 1C, left). However, in a larger proportion of neurons (41%), there was an increase in activity that peaked near the point of learning criterion, when associations were being acquired, and then gradually decreased once the associations were made (FIG. 1C, right).

TABLE 1

Neuronal modulation in the caudate and putamen.

|  | Image | Movement | Feedback | Reward | Any | Total |
| --- | --- | --- | --- | --- | --- | --- |
| Caudate | 35 (23%) | 57 (37%) | 60 (39%) | 61 (40%) | 110 (72%) | 153 |
| Putamen | 18 (28%) | 32 (50%) | 37 (58%) | 28 (43%) | 58 (90%) | 64 |

Each column indicates the number and percent of cells modulated during each time period. the fifth column indicates the number and percent of cells modulated during any (one or more of the four periods.

Neuronal responses during the different periods of the task were further examined as a function of the animals' trial-by-trial performance, or learning curve, and the slope of the this function, or learning rate. The learning rate indicates the rate of change in behavior that occurs during learning. Thus, low rates indicate no change in behavior whereas high rates indicate periods of rapid change in behavior. The learning rate peaks during the steepest portion of the learning curve at which time the animals are actively acquiring new associations between novel images and particular movements (Houk, J. C. et al., MIT Press, Cambridge Mass., 1995; Suri, R. E., & Schultz, W., Neuroscience. 91: 871-980, 1999). Once an association is learned, however, there are no further changes in behavior and the learning rate returns to a low level.

Figure 2:
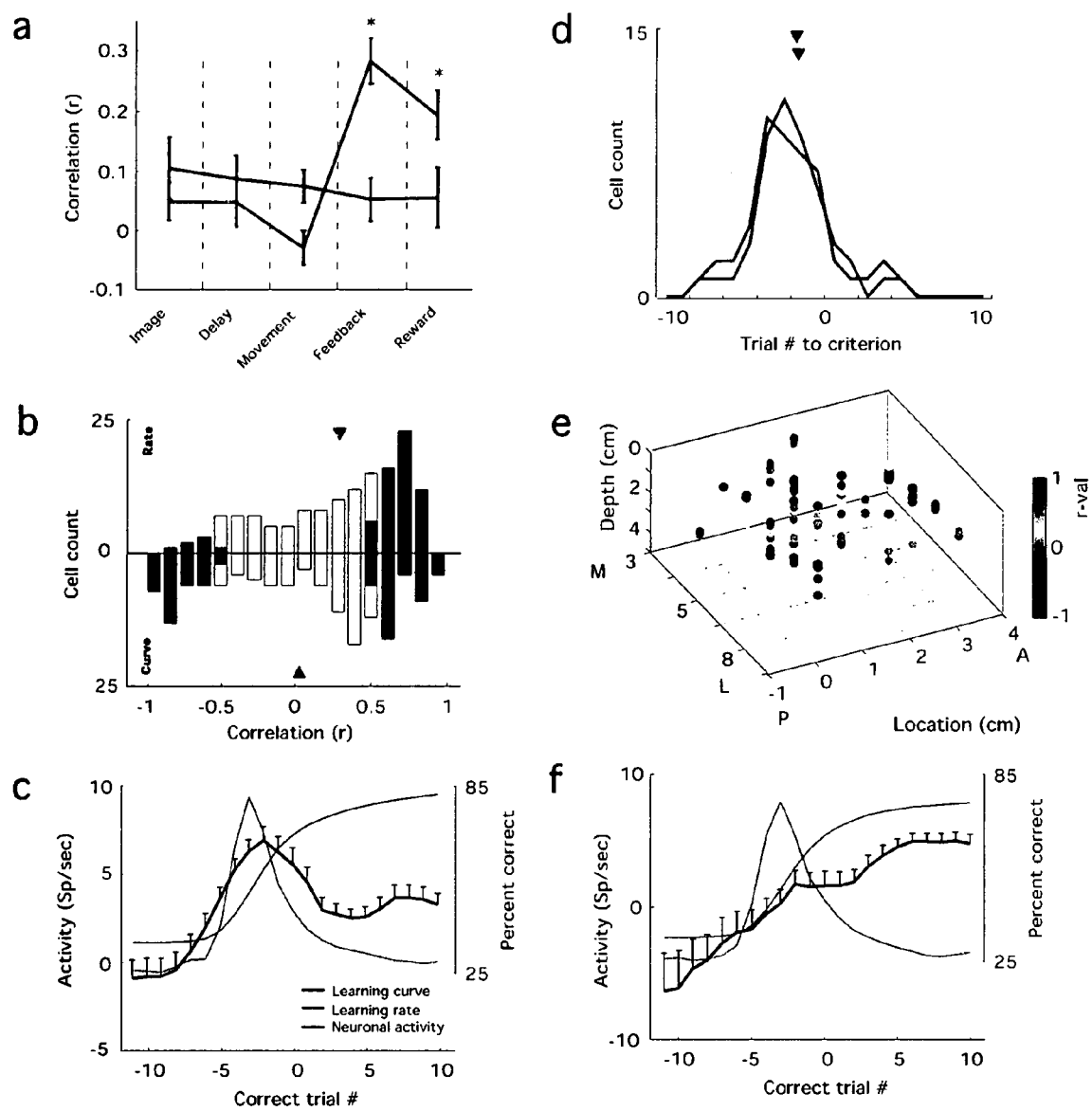
FIG. 2 shows graphs and plots demonstrating population responses during learning.
Figure 3:
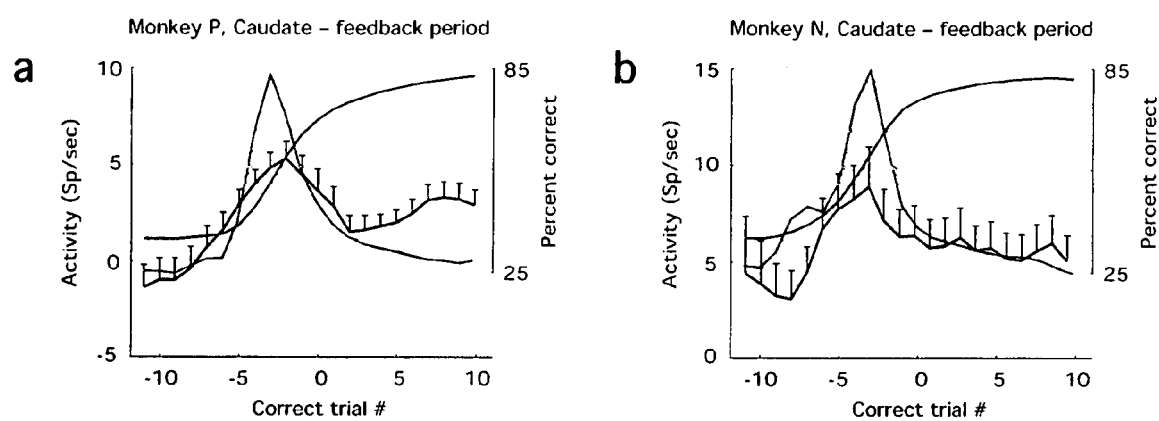
FIG. 3 shows two graphs illustrating population responses during learning for each animal. Mean neuronal activity for the population of caudate cells for each animal, and behavioral performance aligned to learning criterion (trial 0). The blue line represents the learning curve and the red line represents the learning rate, averaged across all trials. The black line represents mean neuronal activity during the feedback period minus baseline, with error bars indicating s.e.m.
Figure 4:
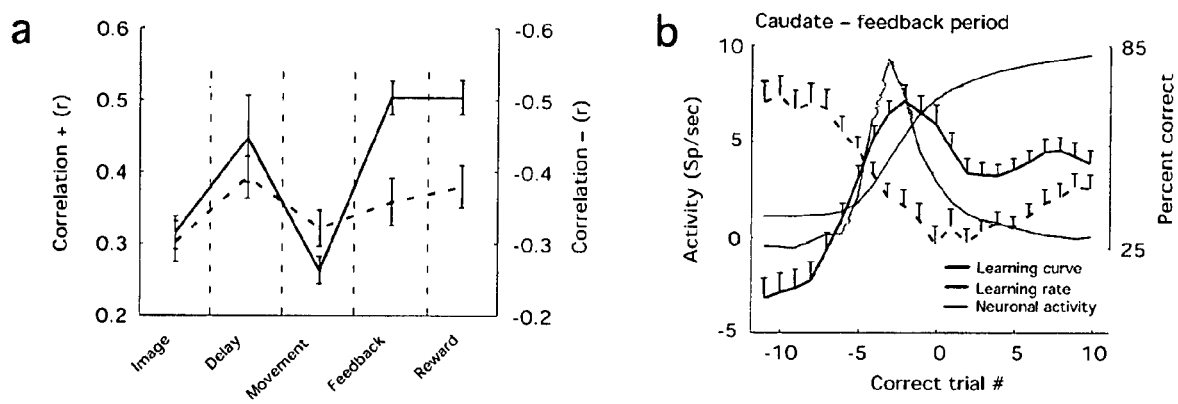
FIG. 4 shows two graphs indicting positively and negatively correlated responses for the population during learning.

Across the population of caudate cells, the most robust learning related changes in activity were found during the feedback period (ANOVA, $p<0.0001$; FIG. 2A). Activity during feedback correlated strongly with the learning rate ($r_r=0.28$; $H_0$: $r=0$, t-test, $p<0.0000001$), and only weakly with the learning curve ($r_c=0.06$, $p>0.05$; FIG. 2B, FIG. 3). This was associated with a larger proportion of cells demonstrating a positive correlation with the rate of learning (FIG. 2C, FIG. 4A, FIG. 4B). In comparison, learning-related activity during image presentation correlated only weakly with either the learning rate ($r_r=0.05$, $p>0.05$), or with the learning curve ($r_c=0.11$, $p<0.05$). On average, neuronal criteria preceded behavioral criteria by 1.8±0.05 trials (FIG. 2D). Learning related changes during feedback were not present for familiar images ($r_r=-0.10$, $r_c=-0.12$, $p>0.05$) or for images in which the animals failed to reach learning criterion ($r_r=0.04$, $r_c=0.06$, $p>0.05$). Learning related changes were also not present for incorrect trials ($r_r=-0.04$, $r_c=0.04$, $p>0.05$). Caudate cells thus tended to exhibit the greatest activity at feedback during the steepest portion of the learning curve when new associations were being acquired, and displayed less activity at the beginning and end of the curve when there was little or no change in learning behavior. Cells with learning rate-related activity were more prevalent anteriorly within the head of the caudate (linear regression, $p<0.01$, FIG. 2E).

In contrast to the caudate, activity of rostral putaminal neurons was more closely correlated with the learning curve rather than the learning rate. Most neurons demonstrated a sustained increase (47%), or a sustained decrease (20%) in activity with learning, whereas a smaller proportion (12%) demonstrated activity that peaked during the steep portion of the learning curve. Across the population, there was a significant correlation with the learning curve during feedback ($r_r=0.39$; $p<0.00001$), and little correlation with the learning rate ($r_r=-0.08$; $p>0.05$; FIG. 2F).

A control task was introduced in 43 caudate cells to test whether the observed responses depended on the animals actively learning the appropriate visual-motor associations. In this task, the sequence of movement directions was 'copied' from the previous block of trials onto a new set of novel images, but the direction of movement was instructed by a color change in one of the targets (O'Doherty, J. et al., Science. 304: 452-454, 2004). Thus, the animals were not required to learn the appropriate motor responses to the new images, but still performed the same sequence of movements and experienced an identical succession of correct and incorrect feedback tones and rewards. In this task, there was no significant correlation between neuronal activity and progression through the sequence of trials ($r_r=-0.06$, $p>0.05$; $r_c=-0.02$, $p>0.05$), whereas the same cells exhibited significant learning rate-related activity in the standard task ($p<0.05$). As in the standard task, there was little correlation between learning performance and neuronal activity on incorrect trials ($p<0.05$).

Learning related responses were not attributable to stimulus novelty. A control task was introduced for 53 cells in which novel images that had been learned in the previous block of trials were reintroduced in the following block but were now associated with a new set of target locations. In these trials, neuronal activity during feedback was again significantly correlated with the rate of learning ($r_r=0.21$, $p<0.01$; $r_c=0.01$, $p>0.05$).

Learning related responses were also not due to simple changes in the frequency or schedule of reward delivery as learning progressed. A control task was used for 23 cells in which an identical sequence of image presentations, cursor movements, feedback and reward delivery from the previous block of trials was replayed to the animals while they maintained fixation without moving the joystick. No peak in activity was found as the animals progressed through these trials ($r_r=0.01$, $p>0.05$) compared to the standard trials ($p<0.05$). Moreover, no correlation was found between learning-related activity during feedback with either arm or eye movements within their target windows (2D Kolmogorov-Smirnov test, $p>0.05$), or licking activity following reward (bootstrap test, $p>0.05$) suggesting that this response pattern was not due to simple changes in motor activity during the task.

Figure 5:
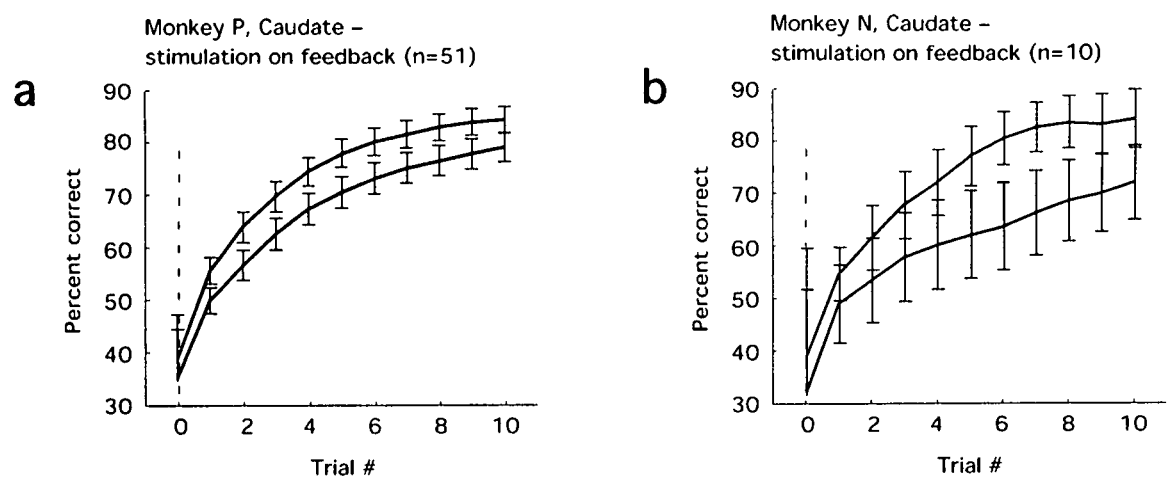
FIG. 5 shows two graphs illustrating the effect of microstimulation on learning performance for each animal. Learning curves are aligned to the first correct trial (0). The top line in FIGS. 5A and B represents mean performance for novel images in which high frequency microstimulation (HFM) was delivered in the caudate following correct responses during the reinforcement period (triggered at feedback). The bottom line in FIGS. 5A and B represents mean performance for novel images in which no stimulation was delivered. Error bars indicate s.e.m.

These findings suggested that neuronal activity in the caudate was closely correlated to the acquisition of new visual-motor associations when change in learning behavior was greatest. Nonetheless, these findings alone did not demonstrate whether the caudate is causally involved in modifying the animals' actual behavior. To test this notion more directly, we used microstimulation (Cohen, M. R. & Newsome, W. T. Curr Opin Neurobiol. 14: 169-177, 2004; Tehovnik, E. J. J Neurosci Methods. 65: 1-17, 1996) in the caudate and putamen. We hypothesized that if the caudate is indeed involved in implementing modifications to the association between sensory cues and motor responses during learning, then introducing microstimulation at the time of reinforcement should enhance or retard the rate at which specific associations are learned. High frequency microstimulation (HFM) was delivered during the feedback-reward period following correct responses for one of the two concurrently learned novel images in each block. As a control, these trial blocks were also interleaved with other blocks in which low frequency microstimulation (LFM) or no stimulation (baseline) was delivered. (FIG. 5)

Figure 6:
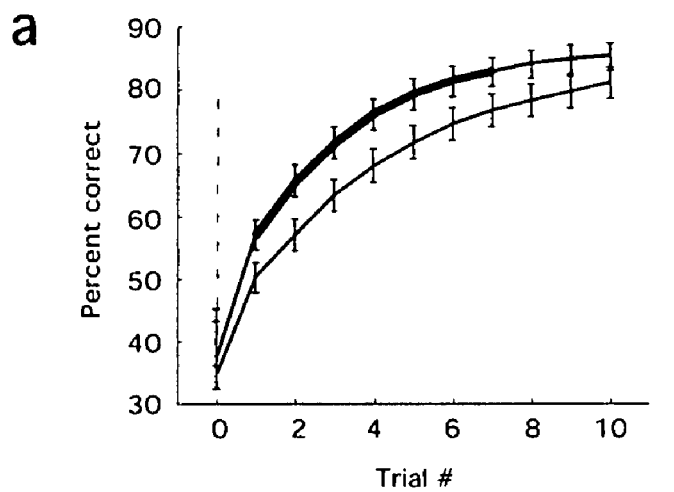
FIG. 6 shows two graphs and a plot indicting the effect of microstimulation on learning performance.
Figure 6:
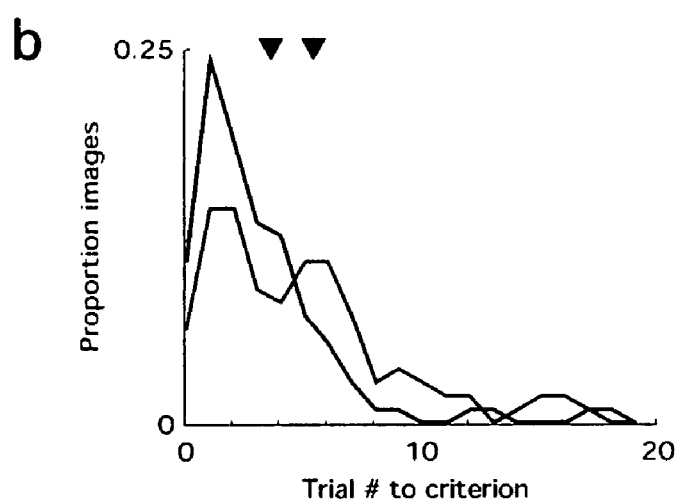
Figure 6:
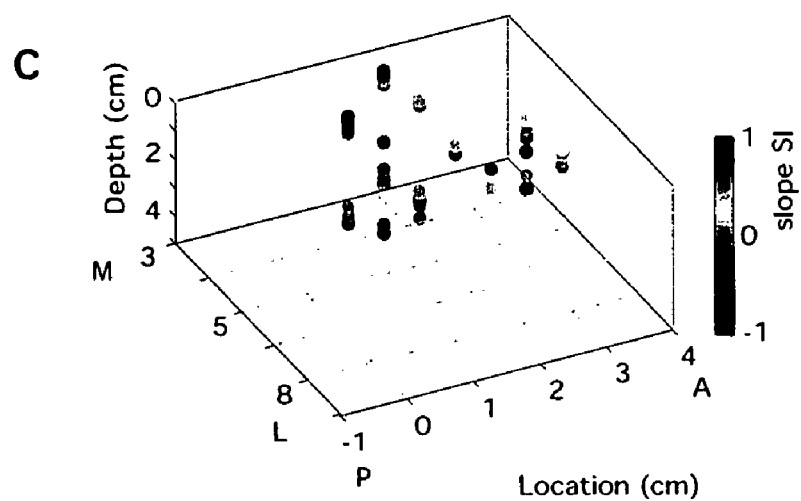
Figure 7:
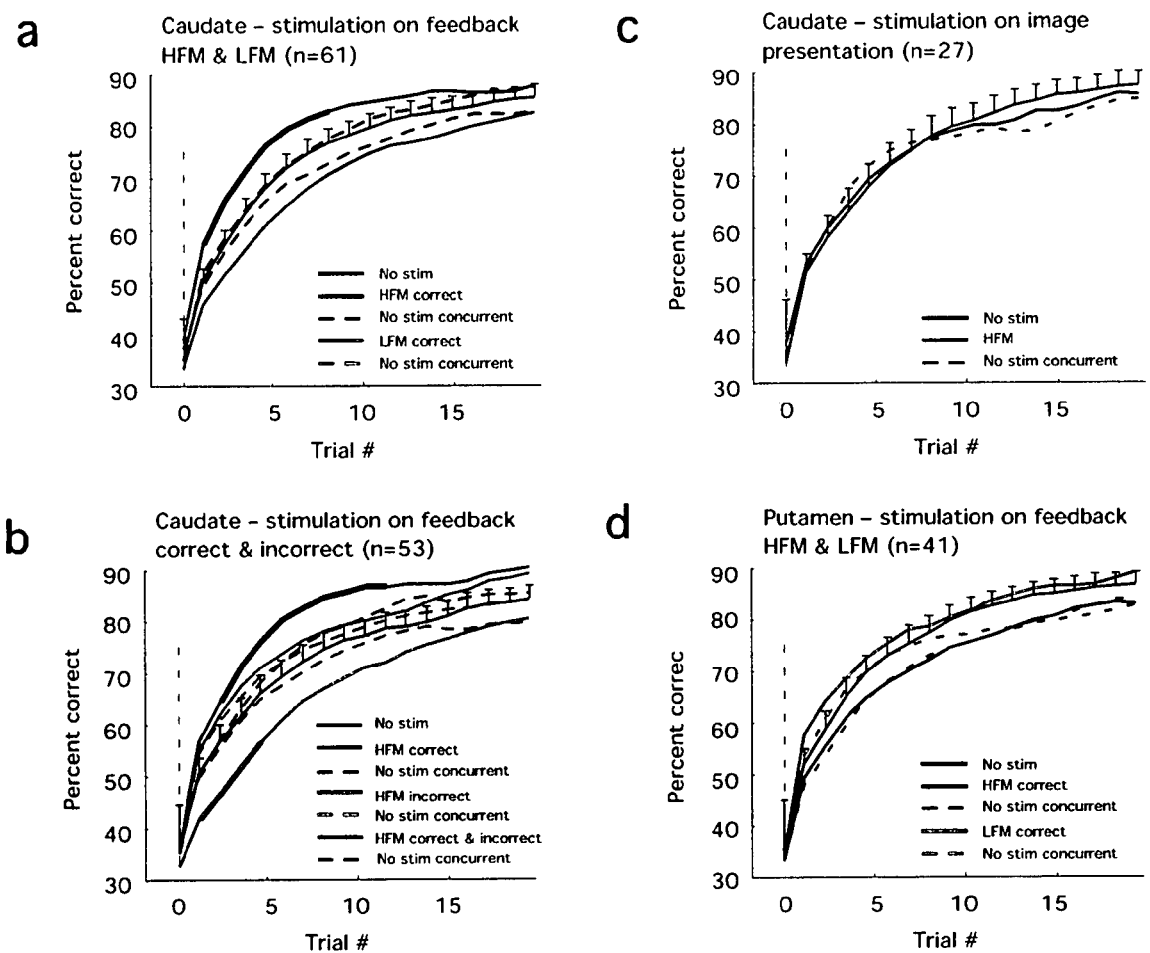
FIG. 7 shows four graphs of results of stimulation controls.

We found that performance on trials in which novel images were coupled with HFM in the caudate was significantly better than on non-stimulated trials (two tailed t-test, incremented comparisons, $p<0.05$; FIG. 6A). This was associated with a significant increase in the steepness, or rate-of-rise, in the animals' learning performance ($SI_r=0.22$; t-test, $p<0.001$). In addition, the animals took significantly fewer trials (30%) to reach learning criteria for stimulated novel images compared to non-stimulated novel images (rank-sum test, $p<0.05$, FIG. 6B). That is, the animals appeared to learn the correct visual-motor associations more quickly and reached learning criteria earlier when correct responses were coupled with HFM during the reinforcement period. The distribution of stimulation sites and corresponding responses within the caudate are displayed in FIG. 6C. There was slight tendency for microstimulation to exert a stronger effect on learning behavior anteriorly within the head of the caudate (linear regression, $p=0.12$). In contrast to its effects on initial learning, HFM had little effect on the animals' final performance at the asymptote once associations had been successfully learned ($SI_{pf}=0.01$; $p>0.05$; FIG. 7A). No significant change in learning performance was found on LFM trials ($SI_r=-0.02$, $SI_{fp}=-0.01$; FIG. 7A).

Each image was associated with a unique movement direction. Hence, it was important to determine whether the improvement in learning could be attributed to a non-specific response bias toward the stimulated target-location. We, therefore, evaluated performance on non-stimulated novel images that were learned concurrently with stimulated images, but corresponded to a different direction of movement. If HFM led to a simple directional bias, then performance would be expected to deteriorate on concurrent non-stimulated trials. We found, however, no difference in the rate of learning ($SI_r=0.06$), or final performance ($SI_{fp}=0.01$) on the non-stimulated trials compared to baseline (FIG. 7A). Similarly, there was no deterioration in performance of familiar trials, indicating that the effect of stimulation was selective for specific associations and did not arise from a non-specific response bias.

Figure 8:
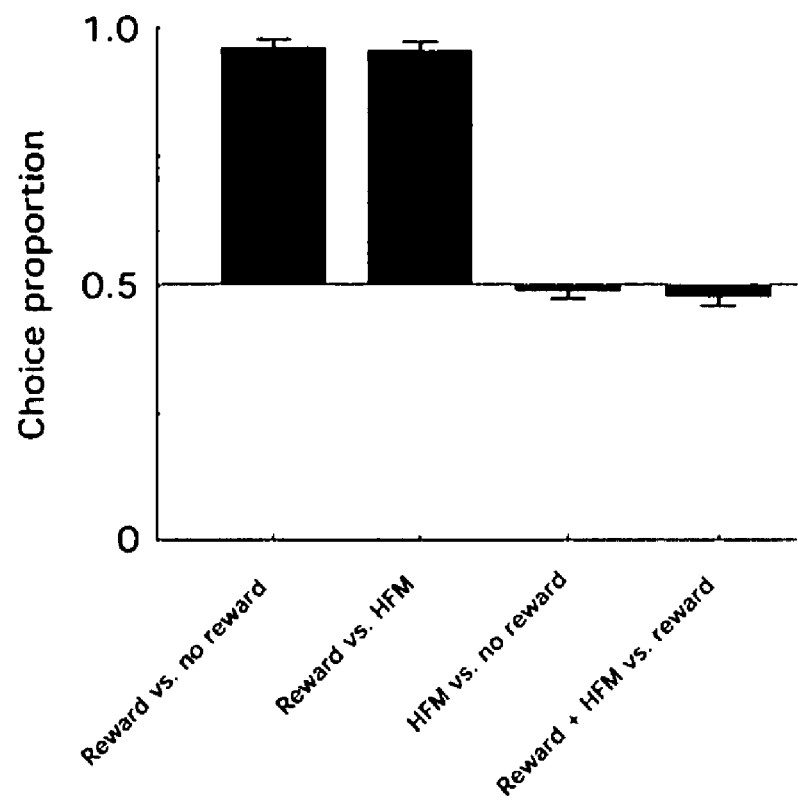
FIG. 8 is a histogram showing results of a paired choice control task. Bars indicate the mean probability (over 18 consecutive trials) of selecting one target over the other, with a choice proportion of 0.5 indicating an equal probability of selecting either target. Error bars indicate s.e.m.

It was also important to determine whether stimulation in the caudate was somehow perceived as being pleasurable. In a separate task, animals were presented with a pair of targets that changed color simultaneously and from which the animals could select freely. Upon reaching the target, the animals would receive either the standard reward, reward with HFM, HFM alone, or neither. No preference was found in target selection for trials in which HFM vs. no HFM was delivered, or for trials in which reward with HFM vs. reward alone was delivered (binomial test, p>0.05; FIG. 8), suggesting that HFM did not lead to a simple hedonic response bias.

Changes in learning performance with stimulation did not appear to result from a general increase in attention or motivational drive. When stimulation was delivered following both correct and incorrect responses, there was no difference in the learning rate ($SI_r$=0.06), or final performance compared to baseline ($SI_{fp}$=0.02; FIG. 7B). When stimulation was delivered on incorrect trials alone, the rate-of-rise in learning performance was significantly blunted ($SI_r$=−0.25, p<0.05), and trial-to-criterion prolonged (rank-sum test, p<0.01; FIG. 7B). Diminished performance was not due to repeated selection of trials in which HFM was delivered, but was rather due to a decreased likelihood of selecting the correct-target location on subsequent trials ($\chi^2$ test, p>0.05). Final performance at the asymptote remained unchanged ($SI_{fp}$=−0.05). Lastly, when stimulation was delivered during the image presentation period in a separate set of trials, no significant effect was found on learning ($SI_r$=−0.01, $SI_{fp}$=0.02; FIG. 7C), indicating that delivery of stimulation in time periods other than reinforcement was not sufficient to alter learning performance.

In comparison to the caudate, there was no enhancement in learning when HFM was delivered in the rostral putamen. Rather, a small non-significant decrease in performance was noted ($SI_r$=−0.16, $SI_{fp}$=−0.01; p>0.05; FIG. 7D), suggesting that the effect of stimulation in enhancing learning was selective to the caudate, and was not generalized to other areas of the dorsal striatum.

Together, these findings suggest that the caudate plays a direct role in augmenting selective visual-motor associations during learning, and that this process likely occurs at the time of reinforcement. Although the precise the mechanisms by which microstimulation exerts its effects are unknown, its influence on learning behavior may be analogous to that of the dopaminergic responses observed with reward. Recent studies have indicated, for example, that delivering tetanic electrical stimulation in the substantia *nigra* can lead to long-term potentiation of activated corticostriatal synapses that are behaviorally relevant[5]. In addition, experiments in striatal slice preparation have demonstrated either long-term potentiation or depression of specific corticostriatal synapses based on the combination of afferent cortical and dopaminergic activity (Wickens, J. R. et al., Curr Opin Neurobiol. 13: 685-690, 2003; Hernandez-Lopez, S. et al., J Neurosci. 17: 3334-3342, 1997). By enhancing dopamine release, high frequency microstimulation in the caudate may similarly result in the potentiation of particular corticostriatal synapses. Alternatively, high frequency microstimulation may act by potentiating activated synapses directly or by altering neuronal firing activity.

While it is unlikely that microstimulation affects learning by precisely mimicking the activity of local neuronal circuitries, we found that delivering microstimulation in the caudate of awake-behaving primates actively performing an associative learning task lead to a significant enhancement in the rate of learning, while having little effect on the animals' final performance. This was consistent with findings made on single unit recordings demonstrating that caudate activity peaked when the change in behavior was greatest—at which time strengthening of associative weights is hypothesized to occur (Houk, J. C. et al., MIT Press, Cambridge Mass., 1995; Suri, R. E., & Schultz, W., Neuroscience. 91: 871-980, 1999). In agreement with the stimulation experiments, moreover, there was little change in activity on final performance, indicating that the caudate likely plays a role in altering the animals' behavior during learning rather than mediating its ultimate acquisition or maintenance.

The notion that the striatum may be involved in associative learning has been supported by human imaging studies demonstrating caudate activation in subjects performing an instrumental conditioning task (O'Doherty, J. et al., Science. 304: 452-454, 2004), and studies in primates demonstrating activity changes correlated with learning (Jog, M. S. et al., Science. 286: 1745-1749, 1999; Hadj-Bouziane, F. & Boussaoud, D., Exp Brain Res. 153: 190-196, 2003; Hollerman, J. R. et al., J Neurophysiol. 80: 947-963, 1998; Kawagoe, R. et al., Nat Neurosci. 1:411-416, 1998; Miyachi, S. et al., Exp Brain Res. 115: 1-5, 1997; Pasupathy, A. & Miller, E. K., Nature. 433: 873-876, 2005). What has been less clear, however, is whether the striatum is involved in implementing adjustments to the associations between sensory cues and the animals' actual motor behavior. These findings suggest that the caudate acts to dynamically enhance or strengthen profitable behavioral policies during learning, thus increasing the organisms' likelihood of selecting actions that lead to reward.

Clinical and Broader Significance

The technique described in this paper can be used to develop interfaces that can be used to facilitate visual-motor associative learning. We already perform deep brain stimulation (DBS) for the treatment of PD, dystonia, tremor and epilepsy. Moreover, there is increasing interest in using DBS to treat Major Depression and Obsessive-Compulsive Disorder. However, to our knowledge, DBS has never been proposed as a tool to enhance learning. Our data suggest that this is quite feasible. Hence it is reasonable to use DBS, or less invasive techniques such as transcranial magnetic or epidural electrical stimulation, to treat brain injuries, learning disorders, or neurodegenerative disorders wherein patients have deficits in the formation of visual-motor associations.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

We claim:

1. A method for increasing the rate of learning in a subject, the method comprising,
   electrically stimulating the striatum in the brain of the subject during an interval of learning in the subject, wherein the interval of learning comprises a reinforcement interval that is a feedback period of learning.

2. The method of claim 1, wherein the learning comprises formation of a visual-motor association.

3. The method of claim 1, wherein stimulating the striatum is stimulating the caudate.

4. The method of claim 1, wherein stimulating the striatum is stimulating the anterior caudate.

5. The method of claim 1, wherein the stimulation of the striatum comprises deep brain stimulation.

6. The method of claim 5, wherein the deep brain stimulation comprises high frequency microstimulation.

7. The method of claim 6, wherein the high frequency microstimulation is at a pulse frequency of about 200 Hz.

8. The method of claim 6, wherein the high frequency micro stimulation is at a phase length of about 0.2 ms.

9. The method of claim 6, wherein the high frequency microstimulation is at an interphase interval of about 0.2 ms.

10. The method of claim 6, wherein the high frequency microstimulation is at an amperage of about 200 μA.

11. The method of claim 6, wherein the high frequency microstimulation comprises a stimulus train of about 1000 ms.

12. The method of claim 1, wherein the stimulation of the striatum comprises epidural electrical stimulation.

13. The method of claim 1, wherein the subject has, has had, or is suspected of having a neurological disease or disorder.

14. The method of claim 13, wherein the neurological disease or disorder is associated with a deficit in learning.

15. The method of claim 13, wherein the neurological disease or disorder is a associated with a deficit in the formation of visual-motor associations.

16. The method of claim 13, wherein the neurological disease or disorder is an associative learning disorder, a brain injury, a neurodegenerative disorder, stroke, epilepsy, autism, or Parkinson's disease.

17. The method of claim 1, wherein the subject is a primate.

18. The method of claim 1, wherein the subject is a human.

* * * * *